(12) United States Patent  (10) Patent No.: US 7,951,977 B2
Ikemoto et al.  (45) Date of Patent: May 31, 2011

(54) PROCESS FOR PRODUCING HEXAHYDROFUROFURANOL DERIVATIVE

(75) Inventors: Tetsuya Ikemoto, Toyonaka (JP); Yosuke Watanabe, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 817 days.

(21) Appl. No.: 11/920,774

(22) PCT Filed: Jun. 5, 2006

(86) PCT No.: PCT/JP2006/311682
§ 371 (c)(1), (2), (4) Date: Nov. 20, 2007

(87) PCT Pub. No.: WO2006/132390
PCT Pub. Date: Dec. 14, 2006

(65) Prior Publication Data
US 2009/0176999 A1  Jul. 9, 2009

(30) Foreign Application Priority Data

Jun. 6, 2005 (JP) .................. 2005-166020
Oct. 14, 2005 (JP) .................. 2005-300487

(51) Int. Cl.
C07C 47/00 (2006.01)
C07C 31/18 (2006.01)
C07D 493/04 (2006.01)

(52) U.S. Cl. ......... 568/442; 568/496; 568/852; 549/464

(58) Field of Classification Search .......... 568/442, 568/496, 852; 549/464
See application file for complete search history.

(56) References Cited

U.S. PATENT DOCUMENTS
2004/0162340 A1  8/2004  Ikemoto et al.

FOREIGN PATENT DOCUMENTS
EP       1 589 018 A1    10/2005
JP       2005-8530 A      1/2005
WO      WO-03/089396 A1  10/2003
WO      WO-2004/033462 A2  4/2004

OTHER PUBLICATIONS

A.B. Northrup et al., "The First Direct and Enantioselective Cross-Aldol Reaction of Aldehydes," Jouranl of American Chemical Society, vol. 124, No. 24, pp. 6798-6799, 2002.
R.I. Storer et al., "Enantioselective organocatalytic aldehyde-aldehyde cross-aldol couplings. The broad utility of α-thioacetal aldehydes," Tetrahedron, vol. 60, No. 35, pp. 7705-7714, 2004.
A.B. Northrup et al., "Enantioselective Organocatalytic Direct Aldol Reactions of α-Oxyaldehydes: Step One in a Two-Step Synthesis of Carbohydrates," Angewandte Chemie International Edition, vol. 43, No. 16, pp. 2152-2154, 2004.
Supplementary European Search Report issued on Nov. 10, 2009 in corresponding European Patent Application No. EP 06747271.2.

*Primary Examiner* — Sikarl A Witherspoon
(74) *Attorney, Agent, or Firm* — Birch, Stewart, Kolasch & Birch, LLP

(57) ABSTRACT

The present invention provides; a process for producing a compound (IV) comprising a step of reacting a compound (I) with a compound (II) in the presence of an optionally substituted cyclic secondary amine to obtain a compound (III) and a step of sequentially or simultaneously eliminating $R^1$ and $R^2$ from the compound (III), and then cyclizing the $R^1$- and $R^2$-eliminated compound to obtain the compound represented by the formula (IV); a process for producing a high purity compound (IV); an intermediate thereof; and a process for producing an intermediate.

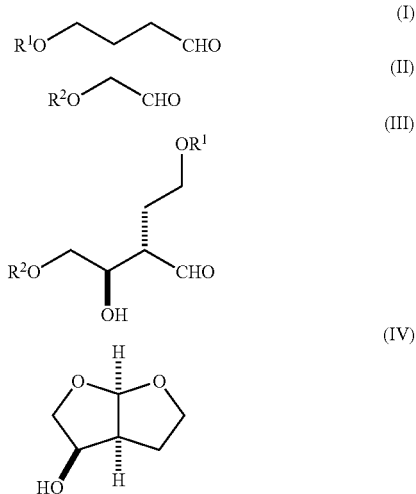

15 Claims, No Drawings

PROCESS FOR PRODUCING HEXAHYDROFUROFURANOL DERIVATIVE

TECHNICAL FIELD

The present invention relates to a process for producing a hexahydrofurofuranol derivative useful as an intermediate in medicine synthesis, a compound useful as the intermediate and a process for producing the same, and a process for purifying a hexahydrofurofuranol derivative.

BACKGROUND TECHNOLOGY

A compound represented by the formula (IV):

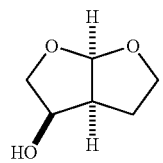

(IV)

(hereinafter, referred to as also compound (IV)), that is, a hexahydrofurofuranol derivative is useful as an intermediate for synthesis of a compound as an anti-AIDS drug (see, WO 01/25240).

As a process for synthesizing a racemic compound represented by the formula (IV), methods described in WO 01/25240, EP 539192-A, WO 2004/002975 and Tetrahedron Letters, 1995, Vol. 36, p. 505 are known. These methods, however, use tributyltin hydride and the like manifesting strong ozone oxidation and toxicity, thus, are not admitted as industrially preferable methods. Further, for obtaining an optically active form thereof (for example, compound represented by the formula (IVa) described later), optical resolution using enzyme is carried out, however, only one of the resulting enantiomers is used for production of an intended substance, and other enantiomer is discarded, leading to inefficiency.

Recently, Tetrahedron Letters, 2001, Vol. 42, p. 2653 suggests a process for directly synthesizing an optically active compound represented by the formula (IVa), and this is the method using an organoselenium compound, thus, it is not admitted as an industrial method.

Further, WO 2004/033462 discloses a method using an optically active form as a raw material, however, the raw material optically active form is expensive, causing an economical problem.

The compound (IV) is usually obtained in the form of a diastereomer mixture with a compound represented by the formula (IV'), however, as an effective method for purifying them, only known are a method of conversion into the corresponding acetate before effecting enzymatic hydrolysis thereof (see, WO 2004/002975), and the like. This method is inefficient since the acetate of the compound represented by the formula (IV') is discarded.

DISCLOSURE OF THE INVENTION

The object of the present invention is to provide a process for producing a compound (IV) (particularly, compound represented by the formula (IVa) as an optically active form thereof) efficiently and inexpensively in industrial scale by a method capable of resolving the problems (for example, use of reagents manifesting strong ozone oxidation and toxicity) of conventional production processes.

Another object of the present invention is to provide a useful intermediate to be used in the above-described process and a process for producing the same.

Further another object of the present invention is to provide a process for producing a high purity compound (IV).

The present inventors have intensively studied to solve the above-described problems, leading resultantly to completion of the present invention.

That is, the present invention is as described below.

<1> A compound represented by the formula (III)

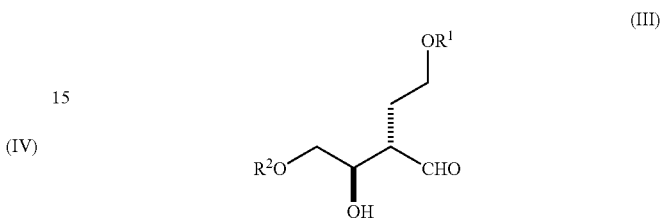

(III)

wherein $R^1$ and $R^2$ each independently show a protective group for hydroxyl group (hereinafter, referred to as compound (III) in some cases).

<2> The compound according to <1>, wherein the compound is the one specified by the formula (IIIa)

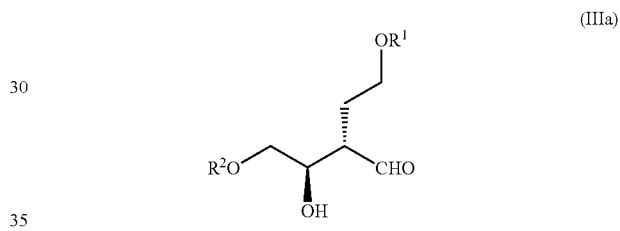

(IIIa)

wherein $R^1$ and $R^2$ have the same meanings as defined above (hereinafter, referred to as compound (IIIa) in some cases).

<3> A compound represented by the formula (III')

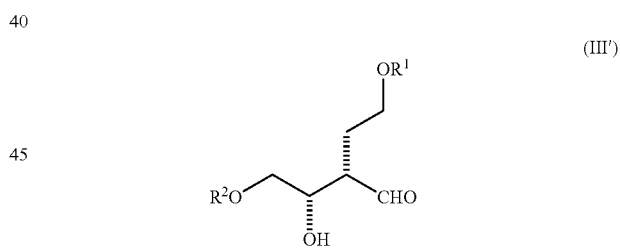

(III')

wherein $R^1$ and $R^2$ each independently show a protective group for hydroxyl group (hereinafter, referred to as compound (III') in some cases).

<4> The compound according to <3>, wherein the compound is the one specified by the formula (III'a)

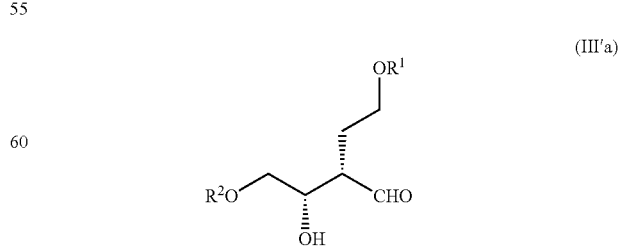

(III'a)

wherein $R^1$ and $R^2$ have the same meanings as defined above (hereinafter, referred to as compound (III'a) in some cases).

<5> A process for producing a compound (III) which comprises reacting a compound represented by the formula (I)

wherein R¹ shows a protective group for hydroxyl group (hereinafter, referred to as compound (I) in some cases), with a compound represented by the formula (II)

wherein R² shows a protective group for hydroxyl group (hereinafter, referred to as compound (II) in some cases), in the presence of an optionally substituted cyclic secondary amine.

<6> The process according to <5>, wherein the optionally substituted cyclic secondary amine is a compound represented by the formula (V)

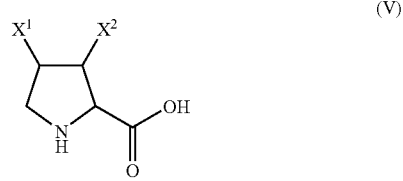

wherein $X^1$ and $X^2$ each independently show a hydrogen atom, hydroxyl group or $OR^3$,
wherein $R^3$ shows a protective group for hydroxyl group (hereinafter, referred to as compound (V) in some cases).

<7> The process according to <6>, wherein the optionally substituted cyclic secondary amine is a compound represented by the formula (Va)

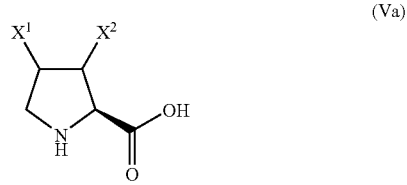

wherein $X^1$ and $X^2$ have the same meanings as defined above (hereinafter, referred to as compound (Va) in some cases), and the compound (III) is a (IIIa).

<8> A process for producing a compound represented by the formula (IV) which comprises sequentially or simultaneously eliminating R¹ and R² from a compound (III), and then
cyclizing the R¹- and R²-eliminated compound.

<9> The process according to <8>, wherein the compound (III) is a compound (IIIa), and the compound (IV) is a compound represented by the formula (IVa):

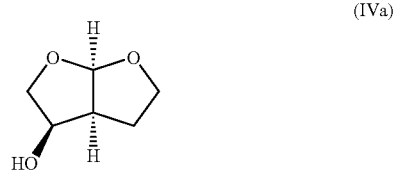

(hereinafter, referred to as compound (IVa) in some cases).

<10> A process for producing a compound (IV) which comprises a step of reacting a compound (I) with a compound (II) in the presence of an optionally substituted cyclic secondary amine to obtain a compound (III); and a step of sequentially or simultaneously eliminating R¹ and R² from the above-described compound (III) and then cyclizing the R¹- and R²-eliminated compound to obtain the compound (IV).

<11> The process according to <10>, wherein the optionally substituted cyclic secondary amine is a compound (V).

<12> The process according to <10>, wherein the optionally substituted cyclic secondary amine is a compound (Va), the compound (III) is a compound (IIIa), and the compound (IV) is a compound (IVa).

<13> A process for producing a high purity compound (IV) which comprises a step of oxidizing a mixture comprising a compound (IV) and a compound represented by the formula (IV')

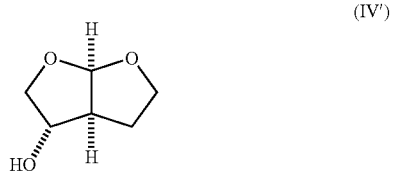

(hereinafter, referred to as compound (IV') in some cases) to obtain a compound represented by the formula (VI)

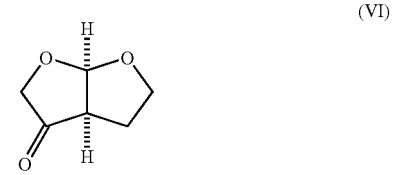

(hereinafter, referred to as compound (VI) in some cases); and a step of reducing the compound (VI) to obtain the high purity compound (IV).

<14> The process according to <13>, wherein the ratio of the compound (IV) in the mixture is 50 to 83% to the total of the compounds represented by the formulae (IV) and (IV'), and the ratio of the high purity compound (IV) is 90% or more.

<15> The process according to <14>, wherein the ratio of the high purity compound (IV) is 95% or more.

<16> The process according to <15>, wherein the ratio of the high purity compound (IV) is 97% or more.

<17> The process according to any one of <13> to <16>, wherein the compound (VI) obtained in the oxidation step is purified by recrystallization, then, the reduction step is conducted.

<18> The process according to <17>, wherein the recrystallization is carried out in an alcohol solvent or ketone solvent.

<19> The process according to <18>, wherein the alcohol solvent or the ketone solvent is at least one kind selected from the group consisting of 2-propanol, methanol, ethanol, t-amyl alcohol, acetone, methyl ethyl ketone and methyl isobutyl ketone.

<20> The process according to <13>, wherein the compound represented by the formula (IV) is a compound (IVa), the compound represented by the formula (IV') is a compound represented by the formula (IV'a)

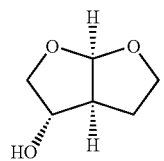

(IV'a)

(hereinafter, referred to as compound (IV'a) in some cases); and the compound (VI) is a compound represented by the formula (VIa)

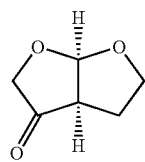

(VIa)

(hereinafter, referred to as compound (VIa) in some cases).

<21> The process according to <20>, wherein the ratio of the compound (IVa) in the mixture is 50 to 83% to the total of the compounds represented by the formulae (IVa) and (IV'a), and the ratio of the high purity compound (IVa) is 90% or more.

<22> The process according to <21>, wherein the ratio of the high purity compound (IVa) is 95% or more.

<23> The process according to <22>, wherein the ratio of the high purity compound (IVa) is 97% or more.

<24> The process according to any one of <13> to <23>, wherein the oxidation is carried out in the presence of 2,2,6,6-tetramethylpiperidinyl-1-oxy or a derivative thereof.

<25> The process according to any one of <20> to <24>, wherein the compound (VIa) obtained in the oxidation step is purified by recrystallization, then, the reduction step is conducted.

<26> The process according to <25>, wherein the recrystallization is carried out in an alcohol solvent or ketone solvent.

<27> The process according to <26>, wherein the alcohol solvent or the ketone solvent is at least one kind selected from the group consisting of 2-propanol, methanol, ethanol, t-amyl alcohol, acetone, methyl ethyl ketone and methyl isobutyl ketone.

<28> The process according to any one of <13> to <27>, wherein the mixture comprising a compound (IV) and a compound (IV') is obtained by a step of reacting a compound (I) with a compound (II) in the presence of an optionally substituted cyclic secondary amine to obtain a mixture comprising a compound (III) and a compound (III'); and a step of sequentially or simultaneously eliminating $R^1$ and $R^2$ from the compound (III) and the compound (III') in the mixture and then cyclizing the $R^1$- and $R^2$-eliminated compounds to obtain the mixture comprising a compound (IV) and a compound (IV').

<29> The process according to <28>, wherein the optionally substituted cyclic secondary amine is a compound (V).

<30> The process according to any one of <20> to <27>, wherein the mixture comprising a compound (IVa) and a compound (IV'a) is obtained by a step of reacting a compound (I) with a compound (II) in the presence of a compound (Va) to obtain a mixture comprising a compound (IIIa) and a compound (III'a); and a step of sequentially or simultaneously eliminating $R^1$ and $R^2$ from the compound (IIIa) and the compound (III'a) in the mixture and then cyclizing the $R^1$- and $R^2$-eliminated compounds to obtain the mixture comprising a compound (IVa) and a compound (IV'a).

<31> A process for producing a compound (VI) which comprises oxidizing a mixture comprising a compound (IV) and a compound (IV')<

<32> The process according to <31>, wherein the compound (IV) is a compound (IVa), the compound (IV') is a compound (IV'a), and the compound (VI) is a compound (VIa).

<33> The process according to <31> or <32>, wherein the oxidation is carried out in the presence of 2,2,6,6-tetramethylpiperidinyl-1-oxy or a derivative thereof.

<34> The process according to any one of <31> to <33>, wherein the compound (VIa) obtained is purified by recrystallization.

<35> The process according to <34>, wherein the recrystallization is carried out in an alcohol solvent or ketone solvent.

<36> The process according to <35>, wherein the alcohol solvent or the ketone solvent is at least one kind selected from the group consisting of 2-propanol, methanol, ethanol, t-amyl alcohol, acetone, methyl ethyl ketone and methyl isobutyl ketone.

BEST MODES FOR CARRYING OUT THE INVENTION

The present invention will be illustrated in detail below.

The compound (III) is a compound having a relative position, and means a compound (IIIa), a compound represented by the formula (IIIb):

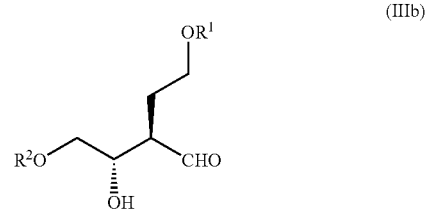

(IIIb)

wherein $R^1$ and $R^2$ have the same meanings as defined above (hereinafter, referred to as compound (IIIb) in some cases), or a mixture of them at any ratio (including racemic form).

Likewise, the compound (III') is a compound having a relative position, and means a compound (III'a), a compound represented by the formula (III'b):

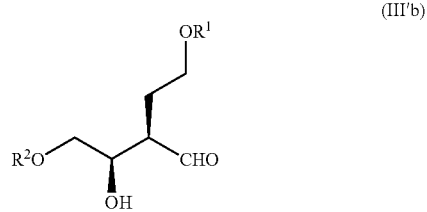

(III'b)

wherein $R^1$ and $R^2$ have the same meanings as defined above (hereinafter, referred to as compound (III'b) in some cases), or a mixture of them at any ratio (including racemic form).

Similarly, the compound (IV) is a compound having a relative position, and means a compound (IVa), a compound represented by the formula (IVb):

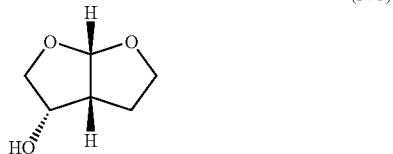
(IVb)

(hereinafter, referred to as compound (IVb) in some cases), or a mixture of them at any ratio (including racemic form).

Further likewise, the compound (IV') is a compound having a relative position, and means a compound (IV'a), a compound represented by the formula (IV'b):

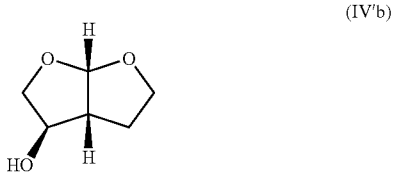
(IV'b)

(hereinafter, referred to as compound (IV'b) in some cases), or a mixture of them at any ratio (including racemic form).

Further similarly, the compound (VI) is a compound having a relative position, and means a compound (VIa), a compound represented by the formula (VIb):

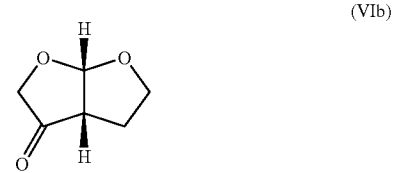
(VIb)

(hereinafter, referred to as compound (VIb) in some cases), or a mixture of them at any ratio (including racemic form).

In the present invention, optically active compounds such as compounds (IIIa), (IIIb), (III'a), (III'b), (IVa), (IVb), (IV'a), (IV'b), (VIa), (VIb), and the like, consist essentially of the optical isomer specified by each structural formula, and can contain 10% by weight or less of, preferably 5% by weight or less of the corresponding enantiomer.

Examples of the protective group for hydroxyl group shown by $R^1$ and $R^2$ include benzyl ether type protective groups such as a benzyl group, 1-phenylethyl group, 1-phenylpropyl group, 1-phenylbutyl group, 2-methyl-1-phenylpropyl group, 1-phenylpentyl group, 2-methyl-1-phenylbutyl group, 3-methyl-1-phenylbutyl group, diphenylmethyl, 1,1-diphenylethyl group, triphenylmethyl, naphthylmethyl, 1-naphthylethyl group and the like; (substituted) alkyl ether type protective groups such as a methyl group, tert-butyl group, 1-ethoxyethyl group, 3,4,5,6-tetrahydro-2H-pyran-2-yl group, 1-methoxy-1-methylethyl group, methoxymethyl group, 2-methoxyethoxymethyl group and the like; silyl type protective groups such as a trimethylsilyl group, triethylsilyl group, tripropylsilyl group, triisopropylsilyl group, tributyl-silyl group, tert-butyldimethylsilyl group, tert-butyldiphenyl-silyl group and the like; ester type protective groups such as an acetyl group, propanoyl group, butanoyl group, isobutanoyl group, pivaloyl group, benzoyl group, 4-nitrobenzoyl group, 4-methoxybenzoyl group, 4-methylbenzoyl group, 4-tert-butylbenzoyl group, 4-fluorobenzoyl group, 4-chlorobenzoyl group, 4-bromobenzoyl group, 3-nitrobenzoyl group, 3-methoxybenzoyl group, 3-methylbenzoyl group, 3-tert-butylbenzoyl group, 3-fluorobenzoyl group, 3-chlorobenzoyl group, 3-bromobenzoyl group, 2-nitrobenzoyl group, 2-methoxybenzoyl group, 2-methylbenzoyl group, 2-tert-butylbenzoyl group, 2-fluorobenzoyl group, 2-chlorobenzoyl group, 2-bromobenzoyl group, 3,5-dinitrobenzoyl group, 3,5-dimethoxybenzoyl group, 3,5-dimethylbenzoyl group, 3,5-di-tert-butylbenzoyl group, 3,5-difluorobenzoyl group, 3,5-dichlorobenzoyl group, 3,5-dibromobenzoyl group, 2,4-dinitrobenzoyl group, 2,4-dimethoxybenzoyl group, 2,4-dimethylbenzoyl group, 2,4-di-tert-butylbenzoyl group, 2,4-difluorobenzoyl group, 2,4-dichlorobenzoyl group, 2,4-dibromobenzoyl group, 2,5-dinitrobenzoyl group, 2,5-dimethoxybenzoyl group, 2,5-dimethylbenzoyl group, 2,5-di-tert-butylbenzoyl group, 2,5-difluorobenzoyl group, 2,5-dichlorobenzoyl group, 2,5-dibromobenzoyl group, 4-phenylbenzoyl group, 2-phenylbenzoyl group, 4-methoxycarbonylbenzoyl group, 3-methoxycarbonylbenzoyl group, 2-methoxycarbonylbenzoyl group and the like; etc., and of them, benzyl ether type protective groups are preferable, and a benzyl group and 1-phenylethyl group are particularly preferable.

As the protective group for hydroxyl group shown by $R^3$, the same protective groups as exemplified for the above-described protective group for hydroxyl group shown by $R^1$ or $R^2$ are mentioned, and a tert-butyldimethylsilyl group is preferable.

"cyclic secondary amine" in "optionally substituted cyclic secondary amine" is a cyclic compound having NH as a ring constitutive atom, and for example, 3 to 8-membered saturated cyclic compounds optionally having, as a ring constitutive atom, further one or two hetero atoms selected from a nitrogen atom, oxygen atom and sulfur atom in addition to NH (e.g., pyrrolidine, piperidine, morpholine, thiomorpholine, piperazine and the like) are mentioned, and of them, pyrrolidine and piperidine are preferable.

Examples of the substituent in "optionally substituted cyclic secondary amine" include a phenyl group, substituted alkyl groups, hydroxyl group, protected hydroxyl groups, carboxyl group and the like. The alkyl group in the substituted alkyl group is preferably an alkyl group having 1 to 6 carbon atoms, and the substituent includes dialkylamino groups (dimethylamino group and the like), acetylamino group, pyrrolidinyl group, piperidinyl group, morpholinyl group, halogen atoms and the like. As the protective group, the same groups as described for $R^1$ and $R^2$ are mentioned. The number of substituents in the optionally substituted cyclic secondary amine is preferably 1 to 3, and when 2 or more, the substituents may be the same or different.

"optionally substituted cyclic secondary amine" is preferably pyrrolidine or piperidine optionally substituted with a substituent selected from a phenyl group, substituted alkyl groups, hydroxyl group, protected hydroxyl groups and carboxyl group, more preferably pyrrolidine or piperidine having a carboxyl group linked to a carbon atom adjacent to NH and optionally substituted with the above-described substituent, further preferably a compound (V). In the compound (V), it is preferable that both $X^1$ and $X^2$ are a hydrogen atom (proline).

In the process of the present invention described later, it is advantageous to use an optically active form of the "optionally substituted cyclic secondary amine" for obtaining an optically active form (for example, compound (IIIa)) of a compound (III). As the optically active form, optically active bodies (for example, compound (Va)) of a compound (V) are preferable, and L-proline is particularly preferable.

The summary of the process of the present invention will be shown in the following scheme.

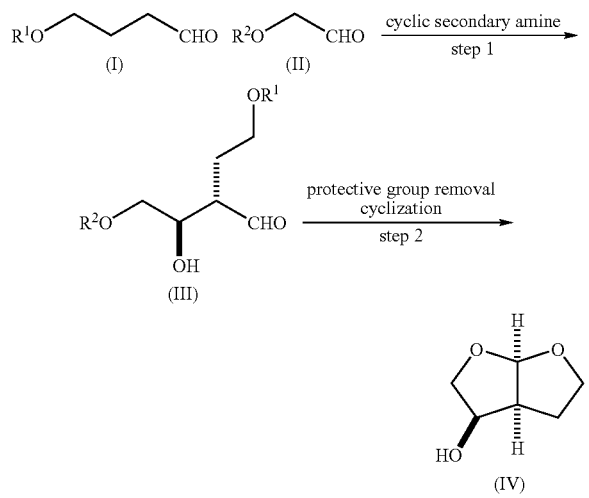

(In the formulae, $R^1$ and $R^2$ have the same meanings as defined above).

The process for producing a compound (IV) of the present invention includes a step of reacting a compound (I) with a compound (II) in the presence of an optionally substituted cyclic secondary amine to obtain a compound (III) as a novel intermediate (step 1); and a step of sequentially or simultaneously eliminating $R^1$ and $R^2$ from the compound (III) and then cyclizing the $R^1$- and $R^2$-eliminated compound to obtain the compound (IV) (step 2).

A description will be made below for each step.
Step 1

The compound (III) can be obtained, for example, by reacting a compound (I) and a compound (II) in a solvent in the presence of an optionally substituted cyclic secondary amine (hereinafter, abbreviated simply as cyclic secondary amine).

Regarding the addition order of a compound (I), compound (II) and cyclic secondary amine, there are mentioned, for example, (1) a method in which a compound (I) and cyclic secondary amine are first dispersed or dissolved in a solvent, and a compound (II) is added to the dispersion/solution, (2) a method in which a compound (II) and cyclic secondary amine are first dispersed or dissolved in a solvent, and a compound (I) is added to the dispersion/solution, (3) a method in which a cyclic secondary amine is first dispersed or dissolved in a solvent, and a compound (I) and compound (II) are added simultaneously to the dispersion/solution, (4) a method in which a compound (I) and compound (II) are first dispersed or dissolved in a solvent, and a cyclic secondary amine is added to the dispersion/solution, and methods combining partially these methods, and the like. Of them, the method (1) or (2) is preferable from the standpoint of increasing reaction selectivity.

The use amount of a compound (II) is usually from 0.1 to 10 mol, preferably 0.3 to 3.3 mol with respect to 1 mol of a compound (I), from the standpoint of economic efficiency.

The use amount of a cyclic secondary amine is usually from 0.1 to 1 mol, preferably 0.15 to 0.4 mol with respect to 1 mol of a compound (I), from the standpoint of effects corresponding to reaction speed and addition amount.

The solvent is not particularly restricted providing it does not disturb the reaction, and examples of preferable solvents include aliphatic hydrocarbon solvents, aromatic solvents, ether solvents, alcohol solvents, ester solvents, water, chlorinated hydrocarbons, aprotic polar solvents, mixed solvents thereof, and the like. Aprotic polar solvents are particularly preferable. The aliphatic hydrocarbon solvent includes n-pentane, n-hexane, isohexane, n-heptane, isoheptane, n-octane, isooctane, n-nonane, isononane, n-decane, isodecane, n-undecane, n-dodecane, cyclopentane, cyclohexane, methylcyclohexane, t-butylcyclohexane, petroleum ether and the like; the aromatic solvent includes benzene, toluene, ethylbenzene, isopropylbenzene, t-butylbenzene, xylene, mesitylene, monochlorobenzene, monofluorobenzene, α,α,α-trifluoromethylbenzene, 1,2-dichlorobenzene, 1,3-dichlorobenzene, 1,2,3-trichlorobenzene, 1,2,4-trichlorobenzene and the like; the ether solvent includes tetrahydrofuran (THF), methyltetrahydrofuran, diethyl ether, di-n-propyl ether, diisopropyl ether, di-n-butyl ether, di-n-pentyl ether, di-n-hexyl ether, di-n-heptyl ether, di-n-octyl ether, t-butylmethyl ether (MTBE), cyclopentyl methyl ether, 1,2-dimethoxyethane, diethylene glycol dimethyl ether, anisole, diphenylether and the like; the alcohol solvent includes methanol, ethanol, 1-propanol, 2-propanol, n-butyl alcohol, isobutyl alcohol, t-butyl alcohol, 1-pentanol, 2-pentanol, isopentyl alcohol, 1-hexanol, 2-hexanol, isohexyl alcohol, 1-heptanol, 2-heptanol, 3-heptanol, isoheptyl alcohol, ethylene glycol monomethyl ether, ethylene glycol monoethyl ether, ethylene glycol mono-n-propyl ether, ethylene glycol monoisopropyl ether, ethylene glycol mono-n-butyl ether, ethylene glycol monoisobutyl ether, ethylene glycol mono-t-butyl ether, diethylene glycol monomethyl ether, diethylene glycol monoethyl ether, diethylene glycol mono-n-propyl ether, diethylene glycol monoisopropyl ether, diethylene glycol mono-n-butyl ether, diethylene glycol monoisobutyl ether, diethylene glycol mono-t-butyl ether and the like; the ester solvent includes ethyl acetate, propyl acetate, isopropyl acetate, buyl acetate, isobuyl acetate, t-butyl acetate, amyl acetate, isoamyl acetate and the like; the chlorinated hydrocarbon includes dichloromethane, chloroform, 1,2-dichloroethane and the like; the aprotic polar solvent includes dimethyl sulfoxide, sulfolane, N,N-dimethylformamide (DMF), N,N-dimethylacetamide, N,N-dimethylpropionamide, N-methylpyrrolidone, γ-butyrolactone, dimethyl carbonate, diethyl carbonate, ethylene carbonate, propylene carbonate, 1,3-dimethyl-2-imidazolidinone, 1,3-dimethyl-3,4,5,6-tetrahydro-2(1H)-pyridinone and the like. Of them, N,N-dimethylformamide or dimethyl sulfoxide is particularly preferable.

The use amount of the solvent is usually 1 to 100 L, preferably 3 to 30 L with respect to 1 kg of a compound (I), from the standpoint of stirring ability and reaction time.

The reaction temperature is usually −30 to 80° C., preferably −10 to 40° C. Further preferably, it is −5 to 25° C. The reaction time is usually 1 to 48 hours depending on the reaction temperature, use amount of a reagent, and the like.

Isolation of compound (III) can be carried out by subjecting a reaction solution to post treatments according to ordinary methods (for example, neutralization, extraction, water washing, distillation, crystallization and the like). Regarding purification, a compound (III) can be purified by recrystallization, extraction purification, distillation, adsorption treatments with activated carbon, silica, alumina and the like; chromatography such as silica gel column chromatography and the like, however, it is also possible that the compound is itself without any purification, for example, the extraction solution itself or the residue itself after solvent distillation, is subjected to the subsequent step.

The compound (III) is often obtained containing a compound (III') as a syn form, in addition to the compound (III) as an intended anti form. In such a case, purification is necessary, and purification may be carried out when a compound (III) is obtained, and it is preferable that purification is carried out after deriving into a compound (IV) (compound (III') is also derived into compound (IV')) from the standpoint of easiness of purification, stability of the compound, and the like.

The compound (III) and the compound (III') are novel compounds, and useful as an intermediate for synthesis of anti-AIDS drugs described in WO 01/025240. Particularly, a compound (IIIa) as an optically active form of the compound (III), and a compound (III'a) as an optically active form of the compound (III') are useful, and of them, the former is particularly useful.

Step 2

The compound (IV) can be obtained by sequentially or simultaneously eliminating protective groups for hydroxyl group ($R^1$ and $R^2$) from the compound (III) and then further cyclizing the $R^1$- and $R^2$-eliminated compound.

The order of removal of $R^1$ and $R^2$ is not particularly restricted, and it may be permissible that $R^1$ is removed first and $R^2$ is removed next, or $R^2$ is removed first and $R^1$ is removed next, or $R^1$ and $R^2$ are removed simultaneously. Simultaneous removal is preferable from the standpoint of decrease in the number of steps.

Removal of $R^1$ and $R^2$ can be carried out by a treatment under conditions suitable for the protective groups according to a usual method. Typical examples thereof will be illustrated below, but the removal method is not limited to them.

Method A

When $R^1$ or $R^2$ is a benzyl ether type protective group such as a benzyl group, 1-phenylethyl group, 1-phenylpropyl group, 1-phenylbutyl group, 2-methyl-1-phenylpropyl group, 1-phenylpentyl group, 2-methyl-1-phenylbutyl group, 3-methyl-1-phenylbutyl group, diphenylmethyl group, 1,1-diphenylethyl group, triphenylmethyl group, naphthylmethyl group, 1-naphthylethyl group and the like, removal of $R^1$ and $R^2$ can be carried out suitably by catalytic hydrogen reduction in the presence of a noble metal catalyst such as palladium carbon, palladium hydroxide and the like. $R^1$ and $R^2$ can be removed suitably also by reaction using an acid catalyst such as Lewis acids such as zinc chloride, aluminum chloride, titanium tetrachloride and the like; proton acids such as hydrochloric acid, sulfuric acid, methanesulfonic acid, p-toluenesulfonic acid, acidic ion exchanged resins and the like, and in this case, the next cyclization reaction can be carried out subsequently. In the present invention, it is preferable that catalytic hydrogen reduction and cyclization are conducted simultaneously in the presence of an acid catalyst and a noble metal catalyst, by combining the above-described two methods.

The use amount of a noble metal catalyst in catalytic hydrogen reduction is usually 0.1 to 500 g, preferably 1 to 100 g in terms of the amount of a noble metal with respect to 1 kg of a compound (III), from the standpoint of effects corresponding to the reaction speed and addition amount.

In the case of catalytic hydrogen reduction, solvents that do not influence the reaction can be used, and preferable examples thereof include ether solvents such as tetrahydrofuran, methyl-t-butyl ether, 1,2-dimethoxyethane, 1,4-dioxane, diglyme and the like; alcohols such as methanol, ethanol, 2-propanol, 1-propanol, 1-butanol, isobutanol, t-butanol and the like; ester solvents such as ethyl acetate, methyl acetate, propyl acetate, isopropyl acetate, butyl acetate and the like; ketones such as acetone, methyl ethyl ketone, methyl isobutyl ketone, 2-octanone, cyclohexanone and the like; organic acids such as acetic acid, propionic acid and the like; water and the like, and the solvent may be a mixture of two or more solvents. The use amount of the solvent is usually 1 to 100 L, preferably 1.2 to 40 L with respect to 1 kg of a compound (III) from the standpoint of stirring ability and reaction time.

The reaction temperature is usually 0 to 120° C., preferably 10 to 60° C. The reaction time is usually 1 to 48 hours depending on the reaction temperature, use amount of a reagent, and the like.

In the case of a reaction using a Lewis acid such as zinc chloride, aluminum chloride and titanium tetrachloride, the use amount is usually 0.8 to 5 mol, preferably 1 to 3 mol with respect to 1 mol of a compound (III), from the standpoint of effects corresponding to the reaction speed and use amount.

In the case of a reaction using hydrochloric acid, sulfuric acid, methanesulfonic acid, p-toluenesulfonic acid and the like among proton acids, the use amount thereof is usually 0.01 to 5 mol, preferably 0.05 to 1 mol with respect to 1 mol of a compound (III) from the standpoint of effects corresponding to the reaction speed and use amount.

In the case of a reaction using an acidic ion exchanged resin among proton acids, the use amount thereof is usually 50 to 500 g, preferably 100 to 300 g with respect to 1 kg of a compound (III) from the standpoint of effects corresponding to the reaction speed and use amount.

In the case of a reaction using the above-described acid catalyst, solvents that do not influence the reaction can be used, and preferable examples thereof include water-soluble solvents such as water, methanol, ethanol, 2-propanol, 1-propanol, 1-butanol, isobutanol, t-butanol, THF, acetone, dioxane and the like, and the solvent may be a mixture of two or more solvents. The use amount of the solvent is usually 0.5 to 100 L, preferably 1 to 40 L with respect to 1 kg of a compound (III) from the standpoint of stirring ability and reaction time.

The reaction temperature is usually 0 to 150° C., preferably 30 to 90° C. The reaction time is usually 1 to 48 hours depending on the reaction temperature, use amount of a reagent, and the like.

When a reaction by catalytic hydrogen reduction and a reaction by an acid catalyst are conducted in combination, examples of preferable solvents include alcohols, esters and ketones mentioned for the above-described reaction by catalytic hydrogen reduction, and the solvent may be a mixture of two or more solvents. The use amounts of a noble metal catalyst and an acid catalyst are the same as in the above-described reaction by catalytic hydrogen reduction and in the case of the above-described reaction by an acid catalyst, respectively, and the reaction temperature and reaction time are the same as in the above-described reaction by catalytic hydrogen reduction.

Method B

When $R^1$ or $R^2$ is a (substituted) alkyl ether type protective group such as a methyl group, tert-butyl group, 1-ethoxyethyl group, 3,4,5,6-tetrahydro-2H-pyran-2-yl group, triphenylmethyl group, 1-methoxy-1-methylethyl group, methoxymethyl group, 2-methoxyethoxymethyl group and the like, $R^1$ and $R^2$ can be removed by reaction of an acid catalyst such as Lewis acids such as zinc chloride, aluminum chloride, titanium tetrachloride and the like; proton acids such as hydrochloric acid, sulfuric acid, methanesulfonic acid, p-toluenesulfonic acid, acidic ion exchanged resins and the like, and the next cyclization reaction can be carried out subsequently. The conditions for this method are the same as described for the method A.

Method C

When $R^1$ or $R^2$ is a silyl type protective group such as a trimethylsilyl group, triethylsilyl group, tripropylsilyl group, triisopropylsilyl group, tributylsilyl group, tert-butyldimethylsilyl group, tert-butyldiphenylsilyl group and the like, $R^1$ and $R^2$ can be removed suitably by reaction with a compound containing a fluorine ion such as tetrabutylammonium fluoride, hydrogen fluoride and the like, and in this case, the next cyclization reaction can be carried out subsequently. $R^1$ and $R^2$ can be removed also by reaction using an acid catalyst such as Lewis acids such as zinc chloride, aluminum chloride, titanium tetrachloride and the like; proton acids such as hydrochloric acid, sulfuric acid, methanesulfonic acid, p-toluenesulfonic acid, acidic ion exchanged resins and the like, and also in this case, the next cyclization reaction can be carried out subsequently. The conditions for the reaction using an acid catalyst are the same as described for the method A.

In the case of a reaction using a compound containing a fluorine ion, the use amount thereof is usually 0.8 to 3 mol, preferably 1 to 1.5 mol with respect to 1 mol of a compound (III) from the standpoint of effects corresponding to the reaction speed and addition amount.

In the case of a reaction using a compound containing a fluorine ion, solvents that do not influence the reaction can be used, and preferable are tetrahydrofuran, methyl-t-butyl ether, 1,4-dioxane, 1,2-dimethoxyethane, diglyme and the like, and the solvent may be a mixture of two or more solvents.

The use amount of the solvent is usually 1 to 100 L, preferably 5 to 30 L with respect to 1 kg of a compound (III) from the standpoint of stirring ability and reaction time.

The reaction temperature is usually −30 to 80%, preferably −10 to 50° C. The reaction time is usually 0.5 to 24 hours depending on the reaction temperature, use amount of a reagent, and the like.

Method D

When $R^1$ or $R^2$ is an ester type protective group such as an acetyl group, propanoyl group, butanoyl group, isobutanoyl group, pivaloyl group, benzoyl group, 4-nitrobenzoyl group, 4-methoxybenzoyl group, 4-methylbenzoyl group, 4-tert-butylbenzoyl group, 4-fluorobenzoyl group, 4-chlorobenzoyl group, 4-bromobenzoyl group, 3-nitrobenzoyl group, 3-methoxybenzoyl group, 3-methylbenzoyl group, 3-tert-butylbenzoyl group, 3-fluorobenzoyl group, 3-chlorobenzoyl group, 3-bromobenzoyl group, 2-nitrobenzoyl group, 2-methoxybenzoyl group, 2-methylbenzoyl group, 2-tert-butylbenzoyl group, 2-fluorobenzoyl group, 2-chlorobenzoyl group, 2-bromobenzoyl group, 3,5-dinitrobenzoyl group, 3,5-dimethoxybenzoyl group, 3,5-dimethylbenzoyl group, 3,5-di-tert-butylbenzoyl group, 3,5-difluorobenzoyl group, 3,5-dichlorobenzoyl group, 3,5-dibromobenzoyl group, 2,4-di-nitrobenzoyl group, 2,4-dimethoxybenzoyl group, 2,4-dimethylbenzoyl group, 2,4-di-tert-butylbenzoyl group, 2,4-difluorobenzoyl group, 2,4-dichlorobenzoyl group, 2,4-dibromobenzoyl group, 2,5-dinitrobenzoyl group, 2,5-dimethoxybenzoyl group, 2,5-dimethylbenzoyl group, 2,5-di-tert-butylbenzoyl group, 2,5-difluorobenzoyl group, 2,5-dichlorobenzoyl group, 2,5-dibromobenzoyl group, 4-phenylbenzoyl group, 2-phenylbenzoyl group, 4-methoxycarbonylbenzoyl group, 3-methoxycarbonylbenzoyl group, 2-methoxycarbonylbenzoyl group and the like, $R^1$ and $R^2$ can be removed suitably with a base such as sodium hydroxide, potassium hydroxide, potassium carbonate and the like. $R^1$ and $R^2$ can be removed suitably also by reaction using an acid catalyst such as Lewis acids such as zinc chloride, aluminum chloride, titanium tetrachloride and the like; proton acids such as hydrochloric acid, sulfuric acid, methanesulfonic acid, p-toluenesulfonic acid, acidic ion exchanged resins and the like. In this case, the next cyclization reaction can be carried out subsequently. The conditions for the reaction using an acid catalyst are the same as described above.

In the case of a reaction using a base such as sodium hydroxide, potassium hydroxide, potassium carbonate and the like, the use amount thereof is usually 0.8 to 5 mol, preferably 1 to 3 mol with respect to 1 kg of a compound (III) from the standpoint of effects corresponding to the reaction speed and use amount.

In the case of a reaction using a base, solvents that do not influence the reaction can be used, and preferable examples thereof include water-soluble solvents such as water, methanol, ethanol, 2-propanol, 1-propanol, 1-butanol, isobutanol, t-butanol, THF, acetone, dioxane and the like, and the solvent may be a mixture of two or more solvents. The use amount of the solvent is usually 1 to 100 L, preferably 3 to 40 L with respect to 1 kg of a compound (III) from the standpoint of stirring ability and reaction time.

The reaction temperature is usually 0 to 150%, preferably 30 to 90° C. The reaction time is usually 1 to 48 hours depending on the reaction temperature, use amount of a reagent, and the like.

Isolation of a compound (IV) can be carried out by subjecting a reaction solution to post treatments according to ordinary methods (for example, neutralization, extraction, water washing, distillation, crystallization and the like).

In the step 1, the compound (III) is obtained containing a compound (III') as a syn form, and when subjected itself to the step 2 without any purification, also the compound (IV) is obtained containing a compound (IV') as a syn form, in addition to the compound (IV) as an intended anti form.

Examples of the method of purifying a compound (IV) in this case include methods usually used for resolution of diastereomers such as recrystallization, extraction purification, distillation (particularly, purification by precision distillation is effective), adsorption treatments with activated carbon, silica, alumina and the like, chromato-methods such as silica gel column chromatography, and the like, and preferably mentioned are purification by silica gel column chromatography and precision distillation.

On the other hand, a high purity compound (IV) can be produced efficiently and easily according to a method shown in the following scheme.

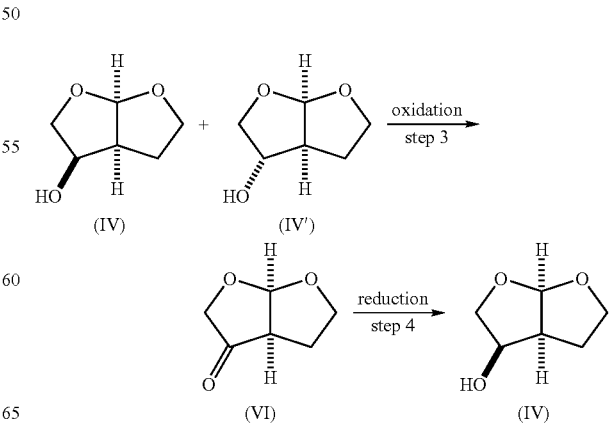

The production process of a high purity compound (IV) of the present invention includes a step of oxidizing a mixture containing a compound (IV) (anti form) and a compound (IV') (syn form) to obtain a compound (VI) (step 3), and step of reducing the compound (VI) to obtain a compound (IV) (step 4). According to this production process, from the above-described mixture containing a compound (IV) in a ratio of about 50 to 83% to the total amount of a compound (IV) and a compound (IV') (compound (IV)/compound (IV')=1/1 to 5/1), a high purity compound (IV) containing the compound (IV) in a ratio of 90% or more, usually 95% or more, preferably 97% or more can be produced.

A description will be made below for each step.

Step 3

The compound (VI) can be obtained, for example, by oxidizing a mixture containing a compound (IV) and a compound (IV'), in a solvent.

The total amount of a compound (IV) and a compound (IV') in the above-described mixture is usually 30% by weight or more, preferably 40% by weight or more, particularly preferably 50% by weight or more in the mixture.

Oxidation of the mixture can be carried out using an oxidizing agent. This oxidation is preferably so-called TEMPO oxidation using TEMPO (2,2,6,6-tetramethylpiperidinyl-1-oxy) or its derivative as a catalyst, from the standpoint of an oxidation method adequately considering cost and environments. In this TEMPO oxidation, a pH regulator can be added according to needs. If necessary, a metal halide or halogenated tetraalkyl quaternary ammonium may be added.

The order of addition of a mixture containing a compound (IV) and a compound (IV'), oxidizing agent, TEMPO or its derivative, pH regulator, and metal halide or halogenated tetraalkyl quaternary ammonium is not particularly restricted. For example, a method is preferable in which a mixture of a mixture containing a compound (IV) and a compound (IV'), TEMPO or its derivative, pH regulator, and metal halide or halogenated tetraalkyl quaternary ammonium is first dispersed or dissolved in a solvent, then, an oxidizing agent is added to the dispersion/solution.

Examples of the oxidizing agent include hypohalous acid salts such as sodium hypochlorite, sodium hypobromite, calcium hypochlorite and the like; organic peracids such as m-chloro perbenzoic acid, t-butyl hydroperoxide, perbenzoic acid and the like; inorganic peracids such as hydrogen peroxide water, potassium hydrogen persulfate and the like; cyanuric halides such as cyanuric chloride and the like; N-halogenated succinic imide such as N-chlorosuccinic imide, N-bromosuccinic imide and the like; N-halogenated hydantoin such as 5,5-dimethyl-1,3-dibromohydantoin and the like; and the like. Of them, hypohalous acid salts, particularly, sodium hypochlorite is preferable from the standpoint of reactivity and cost. The use amount of the oxidizing agent is usually 1 to 8 g equivalent, preferably 1.2 to 4 g equivalent with respect to 1 g equivalent of the total of a compound (IV) and a compound (IV') from the standpoint of effects corresponding to the reaction speed and use amount. The oxidizing agent may be used in the form of aqueous solution.

Examples of TEMPO or derivatives thereof include 2,2,6,6-tetramethylpiperidinyl-1-oxy, 4-hydroxyl-2,2,6,6-tetramethylpiperidinyl-1-oxy, 4-methacryloyloxy-2,2,6,6-tetramethylpiperidinyl-1-oxy, 4-acetamino-2,2,6,6-tetramethylpiperidinyl-1-oxy and the like. Of them, 2,2,6,6-tetramethylpiperidinyl-1-oxy is preferable from the standpoint of reactivity and cost. The use amount of TEMPO or its derivative is usually 0.0001 to 0.1 mol, preferably 0.001 to 0.02 mol with respect to 1 mol of the total of a compound (IV) and a compound (IV') from the standpoint of effects corresponding to the reaction speed and use amount.

Examples of the pH regulator include dipotassium hydrogen phosphate, monopotassium dihydrogen phosphate, disodium hydrogen phosphate, monosodium dihydrogen phosphate, diammonium hydrogen phosphate, monoammonium dihydrogen phosphate, sodium carbonate, sodium hydrogen carbonate and the like. Of them, dipotassium hydrogen phosphate is preferable from the standpoint of reactivity. The use amount of the pH regulator is usually 0.5 to 10 mol, preferably 1.5 to 5 mol with respect to 1 mol of the total of a compound (IV) and a compound (IV') from the standpoint of effects corresponding to the reaction speed and use amount.

Examples of the metal halide or halogenated tetraalkyl quaternary ammonium include potassium iodide, potassium bromide, potassium chloride, sodium iodide, sodium bromide, sodium chloride, tetrabutyl ammonium iodide, tetrabutyl ammonium bromide, tetrabutyl ammonium chloride, trimethylbenzyl ammonium chloride and the like. Of them, potassium bromide and tetrabutyl ammonium bromide are preferable from the standpoint of reactivity. The use amount of the metal halide or halogenated tetraalkyl quaternary ammonium is usually 0.001 to 0.2 mol, preferably 0.01 to 0.1 mol with respect to 1 mol of the total of a compound (IV) and a compound (IV') from the standpoint of effects corresponding to the reaction speed and use amount.

Solvents that do not influence the reaction can be used. Preferable examples thereof include ester solvents such as ethyl acetate, methyl acetate, propyl acetate, isopropyl acetate, butyl acetate and the like; ketone solvents such as acetone, methyl ethyl ketone, methyl isobutyl ketone, cyclohexanone and the like; hydrocarbon solvents such as toluene, xylene and the like; water; and the like, and the solvent may be a mixture of two or more solvents. Of them, ketone solvents are more preferable, and methyl ethyl ketone and methyl isobutyl ketone are particularly preferable.

The use amount of the solvent is usually 3 to 50 L, preferably 5 to 30 L with respect to 1 kg of the total of a compound (IV) and a compound (IV') from the standpoint of stirring ability and reaction time.

The reaction temperature is usually −30 to 60%, preferably −10 to 20° C. The reaction time is usually 1 to 8 hours depending on the reaction temperature, use amount of a reagent, and the like.

Isolation of a compound (VI) can be carried out by subjecting a reaction solution to post treatments according to ordinary methods (for example, neutralization, extraction, water washing, distillation, crystallization and the like). The resultant compound (VI) is itself without any purification, for example, the extraction solution itself or the residue itself after solvent distillation can also be subjected to the subsequent step, however, in the present invention, it is preferable to perform purification to a purity of 90% or more, further 95% or more, particularly 97% or more by recrystallization. As the recrystallization solvent, preferable are alcohol solvents such as 2-propanol, methanol, ethanol, t-amyl alcohol and the like; ketone solvents such as acetone, methyl ethyl ketone, methyl isobutyl ketone and the like, or mixed solvents thereof. The amount of the solvent is 1 L to 50 L, preferably 2 L to 30 L, further preferably 3 L to 15 L with respect to 1 kg of the weight of a coarse compound (VI) before recrystallization. The heat-attainable temperature in recrystallization is usually 40° C. or more and the boiling point under normal pressure of each solvent or less, preferably 50° C. or more and the boiling point under normal pressure of each solvent or less. In this case, it is preferable that the crystal is once dissolved completely, however, complete dissolution is not necessarily needed. Undissolved floating substances may be removed by filtration, however, the removal is not necessarily needed. Around the heat-attainable temperature (heat-attainable temperature minus 10° C. to heat-attainable temperature), the temperature is preferably maintained to a certain extent, and the retention time is usually 10 minutes to 8 hours, preferably 30 minutes to 4 hours. If the temperature is once cooled to temperatures lower by 5° C. to 30° C. than the heat-attainable temperature to find no deposition of a crystal at the temperature, it is preferable that a compound (VI) having a purity of 98% or more is added as a seed crystal in a ratio of about 0.0001% by weight to 1% by weight with respect to the weight of a coarse compound (VI) before recrystallization. Thereafter, the temperature is further cooled down to −30° C. to 25° C., preferably to −10° C. to 15° C., and the resultant crystal is filtrated, thus, a compound (VI) having improved purity can be obtained. The cooling time is usually 1 hour to 24 hours, preferably 3 hours to 15 hours after initiation of cooling.

Step 4

The high purity compound (IV) can be obtained, for example, by reducing a compound (VI) in a solvent.

Examples of the reducing agent include boron hydrides such as sodium boron hydride, potassium boron hydride, tetrabutylammonium boron hydride, sodium triacetoxyboron hydride, lithium tri(sec-butyl)boron hydride, sodium tri(sec-butyl)boron hydride, potassium (sec-butyl)boron hydride and the like; aluminum diisobutyl hydride, lithium aluminum hydride, lithium tri(t-butoxy)aluminum hydride, sodium bis(2-methoxyethoxy)aluminum hydride, diborane, borane-THF complex, borane-dimethyl sulfide complex, aluminum triisopropoxide and the like. Borohydrides, particularly, sodium boron hydride is preferable from the standpoint of economic efficiency, safety and the like.

The use amount of the reducing agent is usually 0.25 to 1.5 mol, preferably 0.25 to 0.5 mol with respect to 1 mol of a compound (VI) from the standpoint of effects corresponding to the reaction speed and use amount.

Solvents that do not influence the reaction can be used, and preferable examples thereof include alcohol solvents such as methanol, ethanol, 2-propanol, 1-propanol, 1-butanol, isobutanol, t-butanol and the like; tetrahydrofuran, methyl t-butyl ether, water and the like. The solvent may be a mixture of two or more solvents. The use amount of the solvent is usually 1 to 100 L, preferably 2 to 50 L with respect to 1 kg of a compound (VI) from the standpoint of stirring ability and reaction time.

The reaction temperature is usually −78 to 50° C., preferably −30 to 30° C. The reaction time is usually 1 to 12 hours depending on the reaction temperature, use amount of a reagent, and the like.

In the step 1, if an optically active form is used as the optionally substituted cyclic secondary amine, an optically active form of a compound (III) is obtained, and if the optically active form of a compound (III) is used in the subsequently step, an optically active form of a compound (IV) is finally obtained. If, for example, a compound (Va) (preferably, L-proline) is used as the optionally substituted cyclic secondary amine, a compound (IIIa) is obtained, and if the compound (IIIa) is used in the subsequent step, a compound (IVa) is finally obtained. In general, the compound (IIIa) may contain an enantiomer (compound (IIIb)) though its optical purity is high (95% ee or more, particularly, 98% ee or more). In such a case, purification can be performed to an optical purity of 98% ee or more, further of 99% ee or more, particularly of 100% ee, by effecting recrystallization after deriving into a compound (VIa) in the step 3.

In the step 1, if, for example, a compound (preferably, D-proline) represented by the formula (Vb)

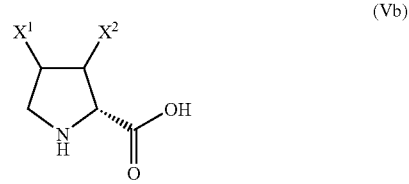

wherein, $X^1$ and $X^2$ each independently show a hydrogen atom, hydroxyl group or $OR^3$ group wherein $R^3$ shows a protective group for hydroxyl group is used as the optionally substituted cyclic secondary amine, a compound (IIIb) is obtained, and if the compound (IIIb) is used in the subsequently step, a compound (IVb) is finally obtained.

The compound (I) as a starting material in the present invention can be produced by a known method. For example, as shown below, it can be produced by protecting one hydroxyl group of 1,4-butanediol to obtain a compound (Ia), then, oxidizing this (for example, oxidation with a hypohalous acid salt such as sodium hypochlorite or the like (preferably, TEMPO oxidation)).

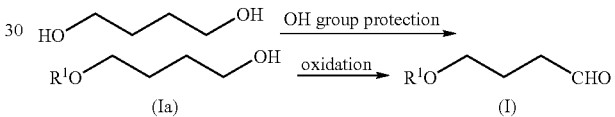

wherein, $R^1$ has the same meaning as defined above.

The compound (II) as another starting material in the present invention can be produced by a known method. For example, as shown below, it can be produced by protecting one hydroxyl group of glycerin to obtain a compound (IIa), then, oxidizing this (for example, oxidation with a periodate such as sodium periodate or the like).

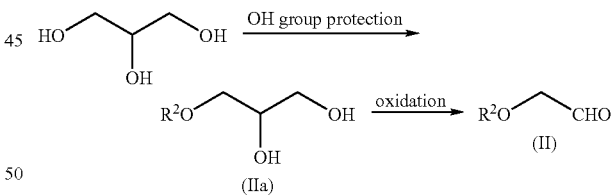

wherein, $R^2$ has the same meaning as defined above.

Alternatively, the compound (II) can be produced also by reacting $R^2OH(R^2$ has the same meaning as defined above) with chloroacetaldehyde dimethylacetal under a base catalyst to obtain $R^2OCH_2CH(OMe)_2$ ($R^2$ has the same meaning as defined above), then, treating this with an acid.

The present invention will be illustrated further specifically by examples below. The present invention is not limited to them at all.

Measurement by GC (gas chromatography) was conducted under the following conditions.

GC Condition:

DB-WAX 30 m×0.53 mm 1 μm, 230° C.

Temperature 100° C. (3 min)→5° C./min→220° C. (13 min) FID

Reference Example 1

Synthesis of 4-benzyloxybutanol

A mixture of toluene (50 ml), 1,4-butanediol (212 g, 2.35 mol) and sodium hydroxide (47.7 g) was heated up to 95° C., and thermally insulated at the same temperature for 30 minutes. Thereafter, benzyl chloride (150 g, 1.185 mol) was added and the mixture was thermally insulated at 95 to 105° C. for 4 hours, then, poured into water (250 ml). After neutralization with 35% hydrochloric acid, the organic layer was liquid-partitioned and the aqueous layer was extracted with toluene (100 ml). The organic layers were combined and washed with saline (100 ml). The organic layer was concentrated under reduced pressure, and the residue was distilled under reduced pressure, to obtain a title compound (115 g, yield 53.8%).

Reference Example 2

Synthesis of 4-benzyloxybutylaldehyde 4-benzyloxybutanol (50 g, 0.277 mol) was dissolved in ethyl acetate (100 ml), and sodium bicarbonate (7 g) and 2,2,6,6-tetramethylpiperidinyl-1-oxy (0.22 g) were added to this, and a 13.8% sodium hypochlorite solution (169 ml) was dropped into this mixture at about 15° C., and the mixture was stirred at the same temperature for 2 hours. The organic layer was washed sequentially with a 5% sodium hypophosphite aqueous solution (50 ml), 5% sodium bicarbonate water (50 ml) and 5% saline (50 ml). The organic layer was concentrated under reduced pressure to obtain a title compound (37.3 g, yield 75.5%).

Reference Example 3

Production of 3-benzyloxy-1,2-propanediol

Into a mixed solution of acetone (800 ml) and glycerin (199 g, 2.16 mol) was added 98% sulfuric acid (6.9 g) at about 25° C., and the mixture was stirred for 3 hours. To this reaction solution was added triethylamine (18.0 g), and the solvent was distilled off under reduced pressure. Into a solution prepared by suspending sodium hydroxide (98.5 g) in toluene (526 ml) was dropped the above-described concentration residue at 55 to 75° C. Into this reaction solution, benzyl chloride (229 g, 1.81 mol) was dropped at 95 to 105%, and the mixture was reacted for 5 hours while distilling components of lower boiling points off. After completion of the reaction, water (366 ml) was added, and the liquid was partitioned. To the resultant toluene layer was added 98% sulfuric acid (22.9 g) and water (571 ml), and the mixture was stirred at about 50° C. for 5 hours stirred, then, the toluene layer was concentrated under reduced pressure. To the residue was added heptane (267 ml), methanol (534 ml) and water (267 ml), and the mixture was liquid-partitioned. The aqueous layer was liquid-partitioned by further adding heptane (267 ml), and the resulting aqueous layer was concentrated under reduced pressure to remove methanol. To the concentrated liquid was added sodium chloride (46 g), and the mixture was extracted twice with ethyl acetate (267 ml). The resultant ethyl acetate solution was concentrated under reduced pressure to obtain a title compound (277 g, yield 84%).

Reference Example 4

Production of 2-benzyloxyacetaldehyde

Into a suspension of water (1055 g) and sodium periodate (406 g) was dropped 3-benzyloxy-1,2-propanediol (366 g, 2.0 mol) at 20 to 25° C. over a period of 21 hours, and the mixture was stirred for 2 hours. Ethyl acetate (495 ml) was added, and the mixture was filtrated and washed. The aqueous layer was extracted with ethyl acetate (825 ml) again, and the organic layers were combined, and washed with a 10% sodium thiosulfate aqueous solution (363 g). The organic layer was treated with phosphoric acid to regulate pH to around 7, then, washed twice with 5% saline (660 g) and dehydrated over anhydrous magnesium sulfate (100 g). Magnesium sulfate was filtrated off, and hydroquinone (1.3 g) was added, the solvent was distilled off, to obtain a title compound (259 g, yield 85.9%).

Example 1

Production of (2S,3R)-4-benzyloxy-2-(benzyloxyethyl)-3-hydroxybutylaldehyde

Under an argon atmosphere, a solution of 2-benzyloxyacetaldehyde (15.0 g, 0.10 mol) in DMF (33 ml) was cooled to 4° C., and L-proline (0.76 g, 6.6 mmol) was added. Thereafter, a solution of 4-benzyloxybutylaldehyde (5.93 g, 0.033 mol) in DMF (33 ml) was dropped over a period of 22 hours, and the mixture was stirred without any modification for 24 hours. After completion of the reaction, extraction was performed by adding 5% saline (300 ml) and ethyl acetate (150 ml), and the aqueous layer was extracted twice with ethyl acetate (150 ml). The organic layers were combined and washed twice with 5% saline (50 ml) and dried over anhydrous sodium sulfate. Sodium sulfate was filtrated, then, the organic layer was concentrated, to obtain a coarse title compound (22.46 g). The resultant (2S,3R)-4-benzyloxy-2-(benzyloxyethyl)-3-hydroxybutylaldehyde was used itself without any purification in the subsequent reaction.

A part (30 mg) of the concentrated residue was purified by flash chromatography, to obtain a pure title compound (5 mg).

$^1$H-NMR (CDCl$_3$, 400 MHz) δ ppm: 9.77 (1H, d, J=2.4 Hz), 7.36-7.28 (10H, m), 4.53 (2H, s), 4.47 (2H, s), 4.12-4.09 (1H, m), 3.57-3.49 (4H, m), 3.03 (1H, d, J=5.4 Hz), 2.68-2.63 (1H, m), 2.14-2.05 (1H, m), 1.92-1.84 (1H, m)

Example 2

Production of (3R,3aS,6aR)-hexahydrofuro[2,3-b]furan-3-ol

The coarse (2S,3R)-4-benzyloxy-2-(benzyloxyethyl)-3-hydroxybutylaldehyde (22.43 g) obtained in Example 1 was dissolved in THF (100 ml). To this was added 10% palladium carbon (50% wet product 10 g) and strong acidic ion exchanged resin (4 g, trade name: Amberlyst 15E, dry product), and the mixture was reacted at room temperature for 22 hours under a hydrogen pressure of 1 atm. Thereafter, palladium carbon and acidic ion exchanged resin were filtrated, and the solvent was distilled off to obtain a brown liquid coarse title compound (9.71 g).

The content of this coarse product was measured by GC (absolute calibration curve method), to find a yield of 53% of the whole diastereomer mixture (yield with respect to 4-benzyloxybutylaldehyde). The diastereomer ratio ((3R,3aS,6aR) form/(3S,3aS,6aR) form) was 4/1.

Further, this coarse liquid (4.63 g) was purified by silica gel chromatography (development solvent; heptane:ethyl acetate=1:3) to obtain a title compound (0.67 g) in the form of colorless transparent liquid. The content was measured by GC (absolute calibration curve method) to find a yield of 29% (yield with respect to 4-benzyloxybutylaldehyde).

The resultant title compound was benzoylated and the optical purity was measured by HPLC, to find that (3R,3aS,6aR)-hexahydrofuro[2,3-b]furan-3-ol was obtained at 99% ee (HPLC analysis condition; column: CHIRALCEL AD 4.6× 250 mm, mobile phase: A hexane, B 2-propanol, A/B=90/10, flow rate: 0.6 ml/min, detector: UV 254 nm).

Example 3

Production of (2S,3R)-4-benzyloxy-2-(benzyloxyethyl)-3-hydroxybutylaldehyde

Under an argon atmosphere, a solution of 2-benzyloxyacetaldehyde (120.1 g, 0.80 mol) in DMF (264 ml) was cooled to 4° C., and L-proline (9.20 g, 80 mmol) was added. Thereafter, a solution of 4-benzyloxybutylaldehyde (71.3 g, 0.40 mol) in DMF (128 ml) was dropped over a period of 22 hours, and the mixture was stirred without any modification for 31 hours. After completion of the reaction, extraction was performed by adding 5% saline (300 ml) and methyl t-butyl ether (300 ml), and the aqueous layer was extracted with methyl t-butyl ether (300 ml). The organic layers were combined and washed with 5% saline (200 ml) and dried over anhydrous sodium sulfate (10 g). Sodium sulfate was filtrated, then, the organic layer was concentrated, to obtain a coarse title compound (193.2 g). The resultant (2S,3R)-4-benzyloxy-2-(benzyloxyethyl)-3-hydroxybutylaldehyde was used itself without any purification in the subsequent reaction.

Example 4

Production of (3R,3aS,6aR)-hexahydrofuro[2,3-b]furan-3-ol

The coarse (2S,3R)-4-benzyloxy-2-(benzyloxyethyl)-3-hydroxybutylaldehyde (193.2 g) obtained in Example 3 was dissolved in ethanol (300 ml). To this was added 10% palladium carbon (50% wet product 8 g) and 5% hydrochloric acid water (30 ml), and the mixture was reacted under a hydrogen pressure of 5 atm at 22 to 33° C. for 19 hours. After completion of the reaction, palladium carbon was filtrated, and potassium carbonate (7.0 g) was added and the mixture was stirred for 1 hour. Thereafter, to an oil obtained by distilling the solvent off was added ethanol (200 ml) and anhydrous sodium sulfate and the mixture was stirred, then, filtrated. The filtrate was concentrated to obtain a brown liquid coarse title compound (98.3 g).

The content of this coarse product was measured by GC (internal standard method), to find a yield of 53% of the whole diastereomer mixture (yield with respect to 4-benzyloxybutylaldehyde). The diastereomer ratio ((3R,3aS,6aR) form/(3S,3aS,6aR) form) was 3.8/1.

Further, this coarse product was purified by distillation under reduced pressure (reduced pressure 0.26 kPa, bath temperature to 140° C., distillation temperature 95 to 105° C.), to obtain 44.2 g of a orange oily title compound (the content by GC (internal standard method) measurement was 53.4% of the whole diastereomer mixture, yield with respect to 4-benzyloxybutylaldehyde; 45.3%)

A part of this was isolated by flash chromatography, and was benzoylated by an ordinary method and the optical purity was measured by HPLC, to find that (3R,3aS,6aR)-hexahydrofuro[2,3-b]furan-3-ol was obtained at 98.8% ee, and (3S,3aS,6aR)-hexahydrofuro[2,3-b]furan-3-ol was obtained at 95.7% ee (HPLC analysis condition; column: CHIRALCEL AD4.6×250 mm, mobile phase: Ahexane, B 2-propanol, A/B=90/10, flow rate: 0.6 ml/min, detector: UV 254 nm).

Example 5

Production of (2S,3R)-4-benzyloxy-2-(benzyloxyethyl)-3-hydroxybutylaldehyde

Under an argon atmosphere, a solution of 2-benzyloxyacetaldehyde (108.1 g, 0.72 mol) in DMF (267 ml) was cooled to 4° C., and L-proline (9.30 g, 80 mmol) was added. Thereafter, a solution of 4-benzyloxybutylaldehyde (71.3 g, 0.40 mol) in DMF (133 ml) was dropped over a period of 6 hours, and the mixture was stirred without any modification for 34 hours. After completion of the reaction, extraction was performed by adding 5% saline (225 ml) and methyl t-butyl ether (200 ml), and the aqueous layer was extracted twice with methyl t-butyl ether (200 ml). The organic layers were combined and washed twice with 5% saline (200 ml) and dried over anhydrous sodium sulfate (10 g). Sodium sulfate was filtrated, then, the organic layer was concentrated, to obtain a coarse title compound (193.1 g). The resultant (2S,3R)-4-benzyloxy-2-(benzyloxyethyl)-3-hydroxybutylaldehyde was used itself without any purification in the subsequent reaction.

Example 6

Production of (3R,3aS,6aR)-hexahydrofuro[2,3-b]furan-3-ol

The coarse (2S,3R)-4-benzyloxy-2-(benzyloxyethyl)-3-hydroxybutylaldehyde (6 g) obtained in Example 5 was dissolved in methanol (20 ml). To this was added 10% palladium carbon (50% wet product 2.5 g) and methanesulfonic acid (0.27 g), and the mixture was reacted at room temperature for 24 hours under a hydrogen pressure of 5 atm. After completion of the reaction, palladium carbon was filtrated, and the solvent was distilled off, then, sodium hydrogen carbonate (0.35 g) and methanol (5 ml) were added and the mixture was stirred. Thereafter, the mixture was filtrated and the solvent was distilled off, and to the resultant oil was added ethyl acetate (5 ml) and the mixture was filtrated again, and concentrated to obtain a yellow liquid coarse title compound (2.64 g).

The content of this coarse product was measured by GC (internal standard method), to find a yield of 55% of the whole diastereomer mixture (yield with respect to 4-benzyloxybutylaldehyde). The diastereomer ratio ((3R,3aS,6aR) form/(3S,3aS,6aR) form) was 3/1.

Example 7

Production of (3R,3aS,6aR)-hexahydrofuro[2,3-b]furan-3-ol

The coarse (2S,3R)-4-benzyloxy-2-(benzyloxyethyl)-3-hydroxybutylaldehyde (6 g) obtained in Example 5 was dissolved in methanol (20 ml). To this was added 10% palladium carbon (50% wet product 2.5 g) and p-toluenesulfonic acid mono-hydrate (0.53 g), and the mixture was reacted at room temperature for 24 hours under a hydrogen pressure of 5 atm. After completion of the reaction, palladium carbon was filtrated, and the solvent was distilled off, then, sodium hydrogen carbonate (0.35 g) and ethyl acetate (5 ml) were added and the mixture was filtrated again, and concentrated to obtain a brown liquid coarse title compound (3.46 g).

The content of this coarse product was measured by GC (internal standard method), to find a yield of 55% of the whole diastereomer mixture (yield with respect to 4-benzyloxybutylaldehyde). The diastereomer ratio ((3R,3aS,6aR) form/(3S,3aS,6aR) form) was 3/1.

Example 8

Production of High Purity (3R,3aS,6aR)-hexahydrofuro[2,3-b]furan-3-ol

The mixture (18.9 g) containing (3R,3aS,6aR)-hexahydrofuro[2,3-b]furan-3-ol (7.93 g, 60.9 mmol), (3S,3aS,6aR)-hexahydrofuro[2,3-b]furan-3-ol (2.07 g, 15.9 mmol), (3S,3aR,6aS)-hexahydrofuro[2,3-b]furan-3-ol (0.05 g, 0.4 mmol) and (3R,3aR,6aS)-hexahydrofuro[2,3-b]furan-3-ol (0.05 g, 0.4 mmol) obtained in Example 4 was dissolved in ethyl acetate (112 ml), and dipotassium hydrogen phosphate (27.1 g, 155.3 mmol), potassium bromide (0.5 g, 3.9 mmol) and 2,2,6,6-tetramethylpiperidinyl-1-oxy (61 mg, 0.4 mmol) were added, and the mixture was cooled to 0. Into this was dropped a sodium hypochlorite aqueous solution (123.9 g, effective chlorine concentration 14%, 0.23 mol) at 15° C. or less, and after completion of dropping, the mixture was stirred for 1 hour. After completion of the reaction, 2-propanol (10 ml) was added, and the mixture was stirred for 30 minutes and liquid-partitioned. Further, the aqueous layer was extracted with ethyl acetate (50 ml) and the organic layers were combined, and dried over anhydrous sodium sulfate (1.0 g) added. Sodium sulfate was filtrated, then, the solvent was distilled off, and 2-propanol (30 ml) was added to the concentrated residue and recrystallization was performed, to obtain a pale brown white crystal (3aR,6aR)-tetrahydrofuro[2,3-b]furan-3(2H)-one (7.4 g, purity 98%, yield 73%). At this stage, the enantiomer excess was 100% ee.

(3aR,6aR)-tetrahydrofuro[2,3-b]furan-3(2H)-one (5.0 g, purity 98%, 38.3 mmol) was suspended in ethanol (15 ml) and the suspension was cooled to −15° C., and sodium boron hydride (0.43 g, 11.5 mmol) was added divisionally, and the resultant mixture was stirred for 2 hours. After completion of the reaction, the mixture was neutralized with 35% hydrochloric acid (1.2 g, 11.5 mmol), and the solvent was distilled off. To the concentrated residue was added ethyl acetate (15 ml) and the mixture was concentrated again, and the concentrated residue was dissolved in ethyl acetate (15 ml), and dried over anhydrous magnesium sulfate (1.0 g) added, then, filtrated and concentrated.

To the resultant concentrated residue was added methanol (20 ml), then, the mixture was concentrated to obtain a title compound in the form of colorless to pale yellow oil (4.81 g, yield 96.6%, (3R,3aS, 6aR)-hexahydrofuro[2,3-b]furan-3-ol/(3S,3aS,6aR)-hexahydrofuro[2,3-b]furan-3-ol ratio=98.2/1.8).

Example 9

Production of High Purity (3R,3aS,6aR)-hexahydrofuro[2,3,b]furan-3-ol

A mixture (287 g, content 69.7%, 1.54 mol) containing (3R,3aS,6aR)-hexahydrofuro[2,3,b]furan-3-ol, (3S,3aS,6aR)-hexahydrofuro[2,3,b]furan-3-ol, (3S,3aR,6aS)-hexahydrofuro[2,3,b]furan-3-ol and (3R,3aR,6aS)-hexahydrofuro[2,3,b]furan-3-ol obtained by the same method as in Example 4 was dissolved in methyl ethyl ketone (2000 ml), and to this was added a solution prepared by dissolving dipotassium hydrogen phosphate (937 g, 5.38 mmol) in water (600 ml). To this was added 2,2,6,6-tetramethylpiperidinyl-1-oxy (1.2 g, 7.7 mmol), and the mixture was cooled to about 0° C. A sodium hypochlorite aqueous solution (1490 g, effective chlorine concentration 13.5%, 2.83 mol) was dropped at 15° C. or less, and the mixture was stirred for 1 hour. After completion of the reaction, a 10% sodium thiosulfate aqueous solution (220 ml) was added and the mixture was stirred for 30 minutes and neutralized with 85% phosphoric acid, and liquid-partitioned. Further, the aqueous layer was extracted twice with methyl ethyl ketone (1000 ml) and the organic layers were combined. To the organic layer was added 1.0 g of hydroquinone, and 3000 ml of the solvent was distilled off. To the concentrated residue was added anhydrous magnesium sulfate (30 g), sodium bicarbonate (20 g) and activated carbon (10 g) and the mixture was stirred for 1 hour. Magnesium sulfate, sodium bicarbonate and activated carbon were filtrated, then, 2-propanol (3000 ml) was added, and the solvent (3300 ml) was distilled off, then, recrystallization was carried out to obtain a white crystal (3aR,6aR)-tetrahydrofuro[2,3-b]furan-3(2H)-one (156.5 g, purity 99.5%, yield 79.1%). At this stage, the enantiomer excess was 100% ee.

Into a mixed solution of methanol (25 ml) and 2-propanol (25 ml) was suspended (3aR, 6aR)-tetrahydrofuro[2,3-b]furan-3(2H)-one (10 g, 78.1 mmol), and sodium boron hydride (0.89 g, 23.4 mmol) was added divisionally to this at 0° C. and the mixture was stirred for 1.5 hours. After completion of the reaction, methanol (15 ml) and ammonium chloride (1.17 g, 21.9 mmol) were added and the mixture was stirred, then, the solvent was distilled off. To the concentrated residue was added 2-propanol (40 ml) and the mixture was concentrated again, and 2-propanol (40 ml) was added to this to cause dissolution. Insoluble materials were filtrated, then, concentration was performed to obtain a title compound in the form of yellow oil (9.87 g, yield 97.2%, (3R,3aS,6aR)-hexahydrofuro[2,3,b]furan-3-ol/(3S,3aS,6aR)-hexahydrofuro[2,3,b]furan-3-ol ratio=97.9/2.1).

According to the present invention, a compound (IV) can be produced efficiently and at low cost in industrial scale without using a reagent manifesting strong ozone oxidation and toxicity. If an optically active form is used as an optionally substituted cyclic secondary amine, an optically active form (for example, compound (IVa)) of a compound (IV) can be produced without using means such as optical resolution and the like. Further, the resultant compound (IV) (anti form) can be once oxidized, then, reduced to convert a compound (IV') (syn form) contained as an impurity into a compound (IV), thus, the compound (IV') can be used effectively, and a high purity compound (IV) can be produced efficiently and easily without needing purification by a column.

The instant application claims priority based on JP-A No. 2005-166020 filed on Jun. 6, 2005 and JP-A No. 2005-300487 filed on Oct. 14, 2005 in Japan, the contents of which being incorporated by reference.

Documents including patents and patent applications cited in this specification are herein incorporated to the same extent as if the contents are disclosed in its entirety by citation.

The invention claimed is:
1. A compound represented by the formula (III)

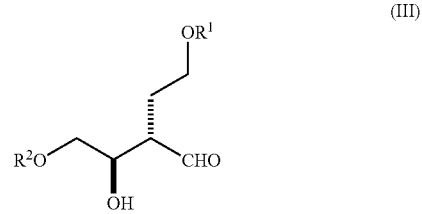

(III)

wherein $R^1$ and $R^2$ each independently show a protective group for hydroxyl group.

2. The compound according to claim 1, wherein the compound is the one specified by the formula (IIIc)

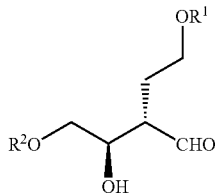
(IIIa)

wherein $R^1$ and $R^2$ have the same meanings as defined above.

3. A compound represented by the formula (III')

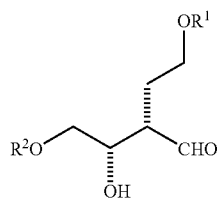
(III')

wherein $R^1$ and $R^2$ each independently show a protective group for hydroxyl group.

4. The compound according to claim 3, wherein the compound is the one specified by the formula (III'a)

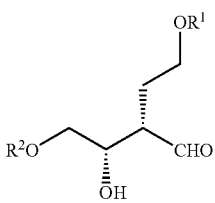
(III'a)

wherein $R^1$ and $R^2$ have the same meanings as defined above.

5. A process for producing a compound represented by the formula (III)

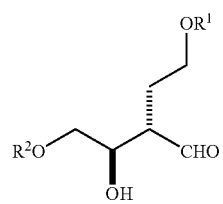
(III)

wherein $R^1$ and $R^2$ each independently show a protective group for hydroxyl group,
which comprises reacting a compound represented by the formula (I)

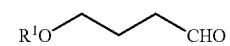
(I)

wherein $R^1$ has the same meaning as defined above, with a compound represented by the formula (II)

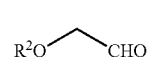
(II)

wherein $R^2$ has the same meaning as defined above,
in the presence of an optionally substituted cyclic secondary amine.

6. The process according to claim 5, wherein the optionally substituted cyclic secondary amine is a compound represented by the formula (V)

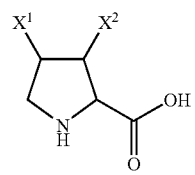
(V)

wherein $X^1$ and $X^2$ each independently show a hydrogen atom, hydroxyl group or $OR^3$,
wherein $R^3$ shows a protective group for hydroxyl group.

7. The process according to claim 6, wherein the optionally substituted cyclic secondary amine is a compound represented by the formula (Va)

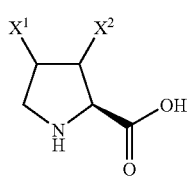
(Va)

wherein $X^1$ and $X^2$ have the same meanings as defined above, and
the compound represented by the formula (III) is a compound represented by the formula (IIIa)

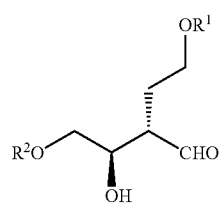
(IIIa)

wherein $R^1$ and $R^2$ have the same meanings as defined above.

8. A process for producing a compound represented by the formula (IV)

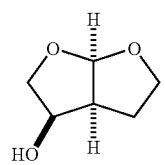
(IV)

which comprises sequentially or simultaneously eliminating R¹ and R² from a compound represented by the formula (III)

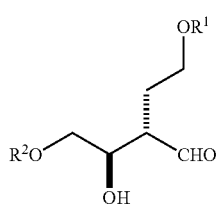
(III)

wherein R¹ and R² each independently show a protective group for hydroxyl group, and then cyclizing the R¹- and R²-eliminated compound.

9. The process according to claim 8, wherein the compound represented by the formula (III) is a compound represented by the formula (IIIa)

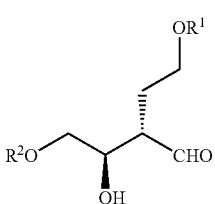
(IIIa)

wherein R¹ and R² have the same meanings as defined above, and
the compound represented by the formula (IV) is a compound represented by the formula (IVa)

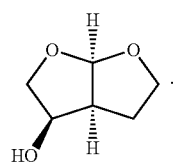
(IVa)

10. A process for producing a compound represented by the formula (IV)

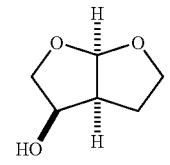
(IV)

which comprises a step of reacting a compound represented by the formula (I)

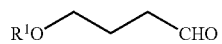
(I)

wherein R¹ shows a protective group for hydroxyl group, with a compound represented by the formula (II)

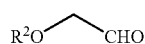
(II)

wherein R² shows a protective group for hydroxyl group, in the presence of an optionally substituted cyclic secondary amine to obtain a compound represented by the formula (III)

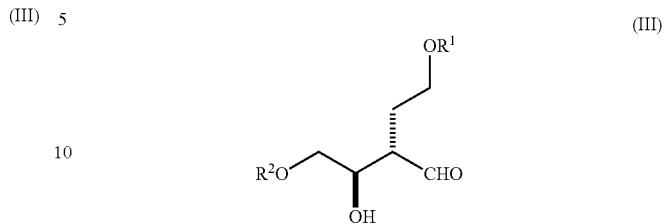
(III)

wherein R¹ and R² have the same meanings as defined above, and a step of sequentially or simultaneously eliminating R¹ and R² from the compound represented by the formula (III), and then cyclizing the R¹- and R²-eliminated compound to obtain the compound represented by the formula (IV).

11. The process according to claim 10, wherein the optionally substituted cyclic secondary amine is a compound represented by the formula (V)

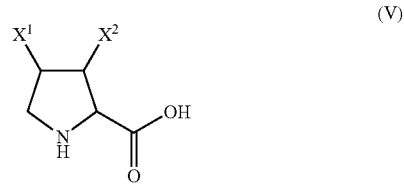
(V)

wherein X¹ and X² each independently show a hydrogen atom, hydroxyl group or OR³,
wherein R³ shows a protective group for hydroxyl group.

12. The process according to claim 10, wherein the optionally substituted cyclic secondary amine is a compound represented by the formula (Va)

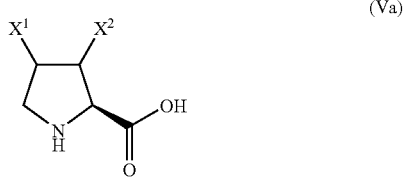
(Va)

wherein X¹ and X² have the same meanings as defined above,
the compound represented by the formula (III) is a compound represented by the formula (IIIa)

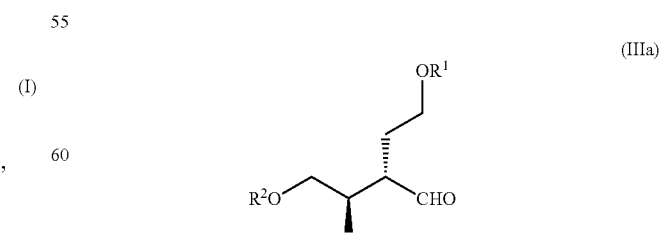
(IIIa)

wherein R¹ and R² have the same meanings as defined above, and the compound represented by the formula (IV) is a compound represented by the formula (IVa)

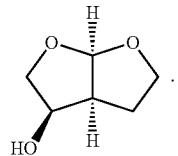
(IVa)

13. A process for producing a high purity compound represented by the formula (IV) which comprises a step of oxidizing a mixture comprising a compound represented the formula (IV)

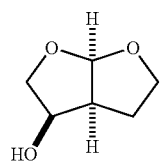
(IV)

and a compound represented by the formula (IV')

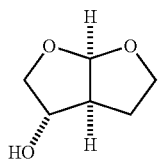
(IV')

to obtain a compound represented by the formula (VI)

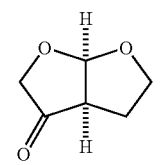
(VI)

and a step of reducing the compound represented by the formula (VI) to obtain the high purity compound represented by the formula (IV)

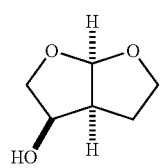
(IV)

wherein the mixture comprising a compound represented the formula (IV) and a compound represented by the formula (IV') is obtained by a step of reacting a compound represented by the formula (I)

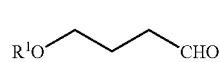
(I)

wherein $R^1$ shows a protective group for hydroxyl group, with a compound represented by the formula (II)

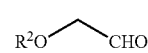
(II)

wherein $R^2$ shows a protective group for hydroxyl group, in the presence of an optionally substituted cyclic secondary amine to obtain a mixture comprising a compound represented by the formula (III)

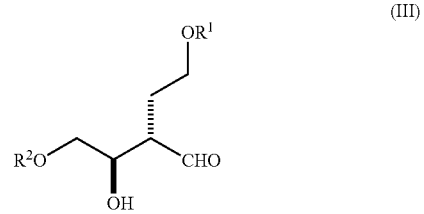
(III)

wherein $R^1$ and $R^2$ have the same meanings as defined above, and a compound represented by the formula (III')

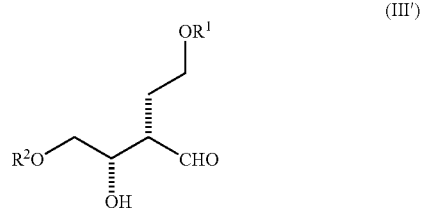
(III')

wherein $R^1$ and $R^2$ have the same meanings as defined above, and a step of sequentially or simultaneously eliminating $R^1$ and $R^2$ from the compounds represented by the formulae (III) and (III') in the mixture, and then cyclizing the $R^1$- and $R^2$-eliminated compounds to obtain the mixture comprising compounds represented by the formulae (IV) and (IV').

14. The process according to claim 13, wherein the optionally substituted cyclic secondary amine is a compound represented by the formula (V)

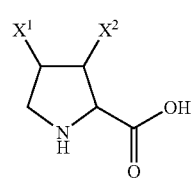
(V)

wherein $X^1$ and $X^2$ each independently show a hydrogen atom, hydroxyl group or $OR^3$, wherein $R^3$ shows a protective group for hydroxyl group.

15. A process for producing a high purity compound represented by the formula (IVa) which comprises a step of oxidizing a mixture comprising a compound represented the formula (IVa)

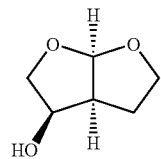
(IVa)

and a compound represented by the formula (IV'a)

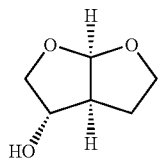
(IV'a)

to obtain a compound represented by the formula (VIa)

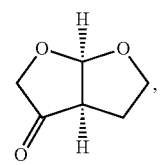
(VIa)

and
a step of reducing the compound represented by the formula (VIa) to obtain the high purity compound represented by the formula (IVa)

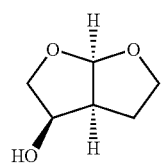
(IVa)

wherein the mixture comprising a compound represented the formula (IVa) and a compound represented by the formula (IV'a) is obtained by a step of reacting a compound represented by the formula (I)

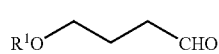
(I)

wherein $R^1$ has the same meaning as defined above, with a compound represented by the formula (II)

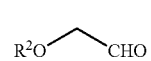
(II)

wherein $R^2$ has the same meaning as defined above, in the presence of a compound represented by the formula (Va)

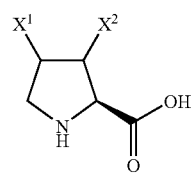
(Va)

wherein $X^1$ and $X^2$ have the same meanings as defined above, to obtain a mixture comprising a compound represented by the formula (IIIa)

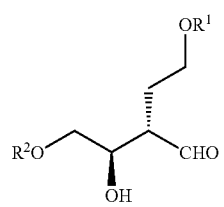
(IIIa)

wherein $R^1$ and $R^2$ have the same meanings as defined above, and a compound represented by the formula (III'a)

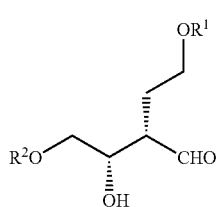
(III'a)

wherein $R^1$ and $R^2$ have the same meanings as defined above, and a step of sequentially or simultaneously eliminating $R^1$ and $R^2$ from the compounds represented by the formulae (IIIa) and (III'a) in the mixture, and then cyclizing the $R^1$- and $R^2$-eliminated compounds to obtain the mixture comprising compounds represented by the formulae (IVa) and (IV'a).

* * * * *